United States Patent [19]

Cavazza

[11] Patent Number: 5,145,871
[45] Date of Patent: Sep. 8, 1992

[54] USE OF ACETYL D-CARNITINE IN THE THERAPEUTIC TREATMENT OF GLAUCOMA, AND PHARMACEUTICAL COMPOSITIONS USEFUL IN SUCH TREATMENT

[75] Inventor: Claudio Cavazza, Rome, Italy

[73] Assignee: Sigma-Tau Industrie Farmaceutiche Riunite S.p.A., Rome, Italy

[21] Appl. No.: 442,702

[22] Filed: Nov. 28, 1989

[30] Foreign Application Priority Data

Dec. 1, 1988 [IT] Italy .................. 48614 A/88

[51] Int. Cl.⁵ .............................................. A61K 31/22
[52] U.S. Cl. ..................................... 514/546; 514/913
[58] Field of Search ..................... 514/546, 913

[56] References Cited

U.S. PATENT DOCUMENTS 4,724,230 2/1988 Cone, Jr. .................. 514/728

OTHER PUBLICATIONS

Int. J. Tiss. Reac., vol. 6, No. 2, 1984, Bioscience Ediprint Inc., Z. Farinella et al.: "Effects of carnitine and acetylcarnitine isomers on mitochondrial respiration", pp. 141–143, see summary Relevant To Claim No. 1,3–8.
Dialog Information Services, File 5, (Biosis), Accession No.: 0019195970, L. Scorolli et al.: "Evaluation of effects of L acetylcarnitine on some functional parameters in a senile glaucomatous patient", & Ann Ottalmol Clin Ocul 114 (9),1988, 927–934, see the whole abstract. Relevant To Claim NO. 1,3–8.
Journal of Pharmaceutical Sciences, vol. 69, No. 9, Sep. 1980, American Pharmaceutical Association, K. W. Reed et al.: "Acetylcarnitine and cholinergic receptors", pp. 1065–1068, see p. 1066: Experimental Relevant To Claim No. 1,3–8.
The Merck Manual of Diagnosis and Therapy, 1987, 15th edition, edited by R. Berkow et al., Merck Sharp & Dohme Research Laboratories, (Rahway, N.J. U.S.), pp. 2234–2240, chapter 224: "Glaucoma" see pp. 2236–2237 Relevant To Claim No. 1,3–8.

*Primary Examiner*—Frederick E. Waddell
*Assistant Examiner*—Zohreh A. Fay
*Attorney, Agent, or Firm*—Oblon, Spivak, McClelland, Maier & Neustadt

[57] ABSTRACT

The use is described of acetyl D-carnitine and its pharmacologically acceptable salts in the therapeutic treatment of glaucoma. The medicament may be administered orally or parenterally or be applied as a collyrium containing approximately 1–10% w/v of acetyl D-carnitine.

6 Claims, No Drawings

USE OF ACETYL D-CARNITINE IN THE THERAPEUTIC TREATMENT OF GLAUCOMA, AND PHARMACEUTICAL COMPOSITIONS USEFUL IN SUCH TREATMENT

This invention relates to a new therapeutic application of acetyl D-carnitine and its pharmacologically acceptable salts in the thereapeutic treatment of glaucoma. The invention further relates to suitable pharmaceutical compositions and particularly a collyrium.

Therapeutic uses of acetyl D,L-carnitine and acetyl L-carnitine are already known. For example, U.S. Pat. No. 4,194,006 describes the use of acetyl carnitine in the therapeutic treatment of ischemia and myocardial arrhythmia. U.S. Pat. No. 4,343,816 describes the use of acetyl carnitine in the therapeutic treatment of functional peripheral vascular diseases of the arteries, such as Raynaud's disease and acrocyanosis. U.S. Pat. No. 4,346,107 describes the therapeutic utility of acetyl carnitine in the treatment of subjects affected by altered cerebral metabolism which is found for example in senile and pre-senile dementia and in Alzheimer's disease. However, there is no correlation between the previously known therapeutic uses of acetyl L-carnitine and that which forms the subject of this invention. Moreover, since the early eighties the therapeutic use of L-carnitine has wholly replaced the sue of D,L-carnitine following the discovery that the D isomer exhibits a harmful antagonizing effect against L-carnitine; it is, therefore, surprising that a D-carnitine derivative exerts an efficacious therapeutic action.

It has, in fact, been shown that D-carnitine is a competitive inhibitor of carnitine-linked enzymes such as carnitine acetyl transferase (CAT) and carnitine palmitoyl transferase (CPT) and that D-carnitine can deplete the L-carnitine level of myocardium and skeletal muscle. Consequently, it is essential that L-carnitine exclusively be administered to patients under medical treatment for heart diseases or regular haemodialytic treatment or lowering of blood lipids, particularly in long term treatments.

Finally, it should be noticed that, prior to the filing date of the present application, no reference has ever been published teaching the use in the ophtalmological field of either carnitine or of any derivative of carnitine, and this regardless of the stereospecific form of the compound.

It has now surprisingly been found that the use of acetyl D-carnitine and its pharmacologically acceptable salts is effective in the therapeutic treatment of glaucoma, a disorder characterized by increased intraocular pressure that may cause impaired vision, ranging from slight loss to absolute blindness. More particularly, it has been found that acetyl D-carnitine and its pharmacologically acceptable salts are useful in the treatment of primary glaucoma (chronic open-angle glaucoma or acute glaucoma or chronic angle-closure glaucoma) or of secondary glaucoma.

This invention accordingly contemplates the use of acetyl D-carnitine and its pharmacologically acceptable salts to produce a pharmaceutical composition for the therapeutic treatment of glaucoma. In practice, approximately 1000 to 2000 mg daily of acetyl D-carnitine or an equivalent quantity of one of its pharmacologically acceptable salts is administered orally or parenterally. Alternatively, or preferably at the same time as the oral or parenteral treatment, a collyrium is administered containing 1-10% w/v of acetyl D-carnitine or an equivalent quantity of its pharmacologically acceptable salts. The collyrium is applied to the extend of 2-3 drops 3-4 times daily.

The pharmaceutical compositions most suitable for oral or parenteral administration are the compositions which in the form of a single dose contain approximately 500 to approximately 1000 mg of acetyl D-carnitine or one of its pharmacologically acceptable salts and a pharmacologically acceptable excipient that is compatible with the active component. Examples of suitable compositions in the form of a single dose are described, for example, in U.S. Pat. No. 4,464,393.

The compositions for the collyrium comprise the usual sterile isotonic solution. The choice of the suitable excipients is within the capabilities of a normally skilled person in pharmaceutical technology. For example, use is made of excipients such as sodium chloride, dibasic sodium phosphate, monobasic potassium phosphate, benzalkonium chloride, and ethyl alcohol. The composition is brought to the correct volume with distilled water.

The activity of acetyl D-carnitine in combating glaucoma has been demonstrated both by means of pharmacological tests in experimental models in vivo and in vitro, and in clinical studies. Some of such tests in experimental models are described below.

EXPERIMENTAL MODEL OF CORTISONE-INDUCED GLAUCOMA

Eight rabbits of the New Zealand breed were used, weighing approximately 2 kg. In the right eye of each animal, 0.8 ml/week of Bentelan Depot (equivalent to 4 mg betametasone) were instilled for 4 weeks. The left eye was kept as control. The medicament, administered subconjunctivally, brought about an increase of the intraocular tension in the first week, reached its peak in the second week and then remained constant until the fifth week.

During the third week of treatment with cortisone, the animals were divided in two groups of four animals each. To the animals of the first group, two drops of a 5% w/v acetyl D-carnitine collyrium were instilled in the right eye, whereas in the left eye two drops of saline were instilled.

The intraocular tension was measured with a Goldman tonometer 1 hour before and 1, 3, 5, 7, 12 and 24 hours following instillations.

A sharp decrease in the intraocular tension of the acetyl D-carnitine treated eyes that was statistically significant versus the saline treated eyes (Student's T test, $P<0.05$), was recorded.

BOLUS OF GLUCOSE-CONTAINING SOLUTION

The model of experimental ocular hypertension in the rabbit induced by a bolus of a glucose-containing solution consisted in the rapid injection of 15 ml/kg body weight of a 5% glucose-containing solution in the marginal vein of the rabbit ear. The injection brought about ocular hypertension which reached its peak ten minutes following injection and subsided after forty minutes. There was no difference in the ocular tension of the two eyes and the tonometric curves were superimposable. For the antihypertensive activity of acetyl D-carnitine to be assessed, the basal tension of either eyeball was measured one hour before injection, then one drop of the medicament was instilled in the right eye and one drop of saline in the left eye. Tonometry was repeated just before injection and at 10, 20, 40 minute-intervals following the end of the injections.

WATER BOLUS

Anaesthetized rabbits were administered an overall amount of 200 ml distilled water at room temperature by oro-gastric intubation. The intraocular tension increased within about one hour and was restored to normal after about three hours. The scope of this model is similar to the previous one.

ADMINISTRATION OF ALPHA-CHYMOTRYPSINE

Intraocular administration of alpha-chymotrypsine (0.5 mg/animal/day) to rabbits for five days brought about an increase of ocular tension liable to become chronic. The scope of this model is similar to the previous one.

In the foregoing experimental models of glaucoma the effects of the administration of acetyl D-carnitine on the intraocular tension were assessed with a pneumotonometer and further controlled with an aplanatic tonometer. Recordings were carried out at standard times for the models of acute glaucoma and every twelve hours for the chronic models.

I claim:

1. A method of treating glaucoma which comprises administering a pharmaceutically effective amount of acetyl D-carnitine or pharmacologically acceptable salts and a pharmacologically acceptable carrier to one in need of treatment.

2. The method in claim 1, wherein said effective amount comprises orally or parenterally administering 1,000 to 2,000 mg/day of acetyl D-carnitine or an equivalent quantity of a pharmacologically acceptable salt.

3. The method of claim 1, comprising administering a collyrium to the eye of a person in need of glaucoma treatment.

4. The method of claim 3, comprising administering a collyrium containing 1–10% w/v of acetyl D-carnitine or an equivalent amount of a pharmacologically acceptable salt thereof and a pharmacologically acceptable carrier.

5. The method of claim 3, wherein said collyrium is a sterile isotonic solution.

6. The method of claim 3, wherein said collyrium further comprises an excipient selected from the group consisting of sodium chloride, dibasic sodium phosphate, monobasic potassium phosphate, benzalkonium chloride and ethyl alcohol.

* * * * *